United States Patent [19]
Kiriki et al.

[11] Patent Number: 6,114,553
[45] Date of Patent: Sep. 5, 2000

[54] SILVER CATALYST FOR PRODUCTION OF ETHYLENE OXIDE, METHOD FOR PRODUCTION THEREOF, AND METHOD FOR PRODUCTION OF ETHYLENE OXIDE

[75] Inventors: Masaharu Kiriki; Hitoshi Takada, both of Kanagawa, Japan

[73] Assignee: Nippon Shokubai Co., Ltd., Japan

[21] Appl. No.: 09/211,382

[22] Filed: Dec. 15, 1998

[30] Foreign Application Priority Data

Dec. 16, 1997 [JP] Japan ................................ 9-345978
Dec. 16, 1997 [JP] Japan ................................ 9-345979

[51] Int. Cl.⁷ ................................................. C07D 301/10
[52] U.S. Cl. ............................................................. 549/534
[58] Field of Search .............................................. 549/534

[56] References Cited

U.S. PATENT DOCUMENTS 4,769,358  9/1988  Kishimoto et al. ...................... 502/348
5,387,751  2/1995  Hayden et al. ......................... 549/534

FOREIGN PATENT DOCUMENTS 0 003 642 A2  8/1979  European Pat. Off. .
47-11467      6/1972  Japan .
53-128594    11/1978  Japan .
59-29291      7/1984  Japan .
05-29501      4/1993  Japan .

*Primary Examiner*—Ba K. Trinh
*Attorney, Agent, or Firm*—Fish & Richardson P.C.

[57] ABSTRACT

A catalyst for the production of ethylene oxide by the vapor phase oxidation of ethylene under specific conditions such that an amount of chlorine suffered to adhere thereto is not more than 2 mol % per mol of silver after the duration of the reaction caused under the specific conditions has totalled 240 hours from the start of the reaction, a silver catalyst for the production of ethylene oxide which incorporates therein an organic nitrogen compound, methods for the production of the catalysts mentioned above, and a method for the production of ethylene oxide by the gaseous-phase oxidation of ethylene with a molecular oxygen-containing gas in the presence of such a catalyst.

9 Claims, No Drawings

SILVER CATALYST FOR PRODUCTION OF ETHYLENE OXIDE, METHOD FOR PRODUCTION THEREOF, AND METHOD FOR PRODUCTION OF ETHYLENE OXIDE

BACKGROUND OF THE INVENTION

1. Field of the Invention

This invention relates to a catalyst for the production of ethylene oxide, a method for the production of the catalyst, and a method for the production of ethylene oxide. It relates more particularly to a silver catalyst which excels in catalytic activity, selectivity, and service life and permits production of ethylene oxide at high selectivity for a long time, a method for the production thereof, and a method for the production of ethylene oxide by the use of this silver catalyst.

2. Description of the Related Art

The production of ethylene oxide by the catalytic vapor phase oxidation of ethylene with a molecular oxygen-containing gas in the presence of a silver catalyst is widely practiced on a commercial scale. Concerning the silver catalyst to be used for the catalytic vapor phase oxidation, numerous inventions covering carriers for the catalyst, methods for depositing the catalyst on such carriers, and reaction promoters used therein have been filed as the patent.

Though the silver catalysts proposed to date are already improved enough to allow high levels of selectivity, the desirability of developing a silver catalyst capable of still higher selectivity finds recognition because an increase of the selectivity even by 1% has a high economic effect in the light of the scale of production of ethylene oxide. By the same token, the improvement in the service life or durability of a silver catalyst brings a high commercial significance.

The mechanism of the deterioration in efficiency of a silver catalyst has not been fully elucidated. A method which improves a silver catalyst effectively in service life has not yet been known to the art.

In the production on a commercial scale of ethylene oxide by the catalytic vapor phase oxidation of ethylene with a molecular oxygen-containing gas in the presence of a silver catalyst, it has been heretofore customary to incorporate in the feed gas for a reaction zone such a gaseous organic chlorine compound as, for example, ethylene dichloride, in an amount generally in the approximate range of 0.1 to 10 ppm for the purpose of improvement in selectivity. The present status of this practice, however, is such that the protracted use of the organic chlorine compound of this sort results in deteriorating the catalyst in performance and eventually shortening the service life of the catalyst.

Our diligent study on the cause for this deterioration, through falling short of definitely elucidating the mechanism thereof, has demonstrated that the adhesion to or the adsorption on the catalyst of the organic chlorine compound in the reaction gas induces the catalyst to suffer from the deterioration. This invention has been perfected on this knowledge.

It has been further found that the adhesion or adsorption of chlorine to or on the catalyst mentioned above can be effectively precluded by having the surface of the catalyst treated with an organic nitrogen compound. This knowledge has brought this invention to perfection.

The practice of using such an organic amine as, for example, ethanolamine, 1,3-propanediamine, ethylenediamine, or an amide in impregnating a carrier for a catalyst with a solution of a silver compound thereby effecting deposition of silver on the carrier has been heretofore known publicly (as disclosed, for example, in U.S. Pat. No. 4,769,358, JP-A-47-11,467, JP-B-59-29,291, JP-B-05-29,501, JP-A-62-114,654, etc.).

The catalyst obtained by utilizing this practice, however, is at a disadvantage in requiring the organic amine to be incorporated in the solution of the silver compound and, as a result, suffering the organic amine to decompose, volatilize, and leave behind substantially no residue in the finished catalyst when the carrier having undergone the impregnation is dried and then calcined. The practice under discussion, therefore, is not effective in preventing the catalyst from adhesion or adsorption of chlorine.

An object of this invention, therefore, is to provide a silver catalyst which excels in catalytic activity, selectivity, and service life and permits production of ethylene oxide at high selectivity for a long time.

Another object of this invention is to provide a method for the production of the silver catalyst mentioned above.

Yet another object of this invention is to provide a method for the production of ethylene oxide by the use of the silver catalyst mentioned above.

SUMMARY OF THE INVENTION

The objects described above are accomplished by a silver catalyst which is intended to produce ethylene oxide by performing the vapor phase oxidation of ethylene such that an amount of chlorine suffered to adhere thereto is not more than 2 mol % per mol of silver after the duration of the reaction caused under the following condition has totalled 240 hours from the start of the reaction:

(Conditions for vapor phase oxidation)

Reaction tube: Made of stainless steel and measuring 25 mm in inside diameter and 6000 mm in length Amount of catalyst loaded: 2.2 liters Reaction pressure: 15 kg/cm$^2$ G Reaction temperature: Such a temperature as attains ethylene conversion, 11 mol %, of Composition of feed gas: Ethylene 20 vol. %, oxygen 0 vol. %, carbon dioxide 7 vol. %, ethane 0.1 vol. %, ethylene dichloride 2.0 ppm, and at least one inert gas selected from among methane, nitrogen, and argon.

Gas hourly space velocity of gas: 6500 hr$^{-1}$.

The objects mentioned above are accomplished by a method for the production of a catalyst used for the production of ethylene oxide, which method comprises causing a catalyst having silver deposited thereon to incorporate therein an organic nitrogen compound.

The objects mentioned above are accomplished by a method for the production of ethylene oxide, which method comprises effecting vapor phase oxidation of ethylene with a molecular oxygen-containing gas in the presence of the silver catalyst mentioned above.

The objects mentioned above are also accomplished by a silver catalyst for the production of ethylene oxide, which catalyst contains an organic nitrogen compound.

The objects mentioned above are accomplished by a method for the production of a silver catalyst intended for producing ethylene oxide, comprising the steps of (a) preparing an aqueous silver-amine complex solution by adding an aqueous amine complex solution to a water slurry containing a silver salt, (b) impregnating a porous carrier with the aqueous silver-amine complex solution and then subjecting the carrier impregnated with the aqueous solution to a heat treatment, (c) impregnating the heat-treated porous carrier with a solution of an organic nitrogen compound and then causing the carrier impregnated with said solution to dry, and further (d) causing the carrier consequently incorporated the organic nitrogen compound to be impregnated with an alkali metal and then drying the resultant wet carrier.

The objects mentioned above are further accomplished by a method for the production of ethylene oxide, which method comprises effecting vapor phase oxidation of ethylene with a molecular oxygen-containing gas in the presence of the silver catalyst mentioned above.

The silver catalyst of this invention enjoys high activity and high selectivity and excels in service life and, therefore, permits production of ethylene oxide at high selectivity for a long time.

This silver catalyst proves highly advantageous from the economic point of view because it elongates the interval of replacement of catalyst so much as to lower the cost of the catalyst and consequently the cost of production of ethylene oxide.

DESCRIPTION OF THE PREFERRED EMBODIMENT

Specifically, the efficiency of the catalyst of this invention is evaluated by a method which comprises preparatorily heating a stainless steel reaction tube, 25 mm inside diameter and 6000 mm in length, provided with an external heating device to a temperature lower than the reaction temperature (within about 50° C. less the reaction temperature), loading the reaction tube with 2.2 liters of the silver catalyst to be evaluated, supplying to this reaction tube a feed gas composed of 20 vol. % of ethylene, 8 mol. % of oxygen, 7 vol. % of carbon dioxide, 0.1 vol. % of ethane, 2.0 ppm of ethylene dichloride, and at least one inert gas selected from among methane, nitrogen, and argon under a pressure of 15 kg/cm$^2$ G at a gas hourly space velocity of 6500 hr$^{-1}$, gradually heating the reaction tube in such a manner that the conversion of ethylene may reach 11 mol. % after the duration of the supply of the feed gas has totalled 192 hours (8 days), thereafter maintaining the temperature of the reaction tube at a level for keeping the conversion of ethylene at 11 mol. %, allowing the reaction to proceed at this reaction temperature for 240 hours (10 days), subsequently removing the catalyst from the reaction tube, and examining the catalyst to measure the amount of chlorine deposited thereon.

The expression used herein in implying "240 hours from the start of the reaction" onward means the duration of 240 hours as reckoned from the time at which the conversion of ethylene attained reaches 11 mol. %.

Incidentally, the conversion of ethylene and the selectivity of ethylene oxide are determined by subjecting the reaction gas emanating from the reaction tube to analysis by means of the gas chromatography.

The silver catalyst of this invention has such a capacity as to attain deposition of not more than 2 mol. %, preferably not more than 1.5 mol. %, and particularly preferably not more than 1 mol. %, of chlorine per mol of silver after the duration of the reaction of vapor phase oxidation of ethylene caused under the conditions mentioned above has totalled 240 hours from the start of the reaction. The silver catalyst which has such a low deposition of chlorine as mentioned above excels in catalytic activity, selectivity, and service life and, therefore, manifests an outstanding catalytic efficiency for a long time.

The amount of chlorine deposited on the catalyst which is contemplated by this invention is determined by dividing the catalyst in the reaction tube after completion of the reaction into five substantially equal portions (five catalyst layers divided as under substantially equally in the direction of length of the reaction tube), extracting these portions sequentially from the reaction tube, measuring the amounts of chlorine deposited on the portions of catalyst by means of a fluorescent X-ray analyzer, averaging the five measurements consequently obtained, and reporting the average as the total amount of chlorine deposited on the whole catalyst.

Conditions for fluorescent X-ray analysis

Bulb used: Cr

Spectral crystal: EDDT

Analytical spectrum: K$\alpha$, $2\theta$=64.94.

The amount of chlorine deposited on a given portion of catalyst is determined by preparing a sample for analysis by pulverizing part of the portion of catalyst and press molding the resultant powder in a prescribed shape, analyzing this sample, and rating the result of analysis relative to a calibration curve formed in advance with an unaltered catalyst impregnated with a known amount of potassium chloride (KCl).

The catalyst which is intended for producing ethylene oxide by effecting the vapor phase oxidation of ethylene so that the amount of chlorine deposited thereon after the duration of the reaction has reached 240 hours from the start of the reaction may total not more than 2 mol. % per mol of silver can be produced by causing the carrier having undergone the deposition of silver to incorporate therein an organic nitrogen compound. The incorporation of the organic nitrogen compound can be attained by various methods such as, for example, impregnation, immersion, spraying, and mixing.

As typical examples of the organic nitrogen compound, amide compounds may be cited. Among other amide compounds, formamide, propionamide, malonamide, lactamide, and urea are used advantageously. These organic nitrogen compounds may be used either singly or in the form of a mixture of two or more members.

Properly, the content of the organic nitrogen compound in the catalyst is such that the atomic ratio of the nitrogen atom (N) to the silver atom (Ag), (N·Ag), may fall in the range of 0.00005:1–0.5:1, preferably in the range of 0.0001:1–0.1:1, and particularly preferably in the range of 0.0005:1–0.05:1. If this content is unduly small, the catalyst will produce only an insufficient effect in preventing the deposition of chloride. Conversely, if the content is unduly large, the initial selectivity of the catalyst will be intolerably low.

The incorporation of the organic nitrogen compound can be basically accomplished by the standard method of making the addition of this organic nitrogen compound at a proper stage in the process for the production of the silver catalyst. To be specific, this incorporation of the organic nitrogen compound may be satisfactorily attained as disclosed in JP-A-62-114,654, for example, by suitably making the addition of the compound during the process of precipitation of reduced metallic silver in the form of minute particles on the inner and outer surfaces of a carrier which occurs in consequence of a procedure comprising the steps of impregnating a porous inorganic carrier represented by $\alpha$-alumina with an aqueous solution prepared by dissolving in water a silver salt such as silver nitrate, silver carbonate, silver acetate, or silver oxalate and a complex-forming agent such as mono-, di- or tri-ethanol amine, drying the impregnated carrier, and then heat-treating the dried carrier in a current of air at a temperature of not more than 400° C., preferably not more than 300° C.

Though typical methods for implementing the incorporation of the organic nitrogen compound will be described below, this invention does not need to discriminate the incorporation on account of the manner of addition. The use of α-alumina as a carrier is assumed herein for the sake of convenience.

(1) α-Alumina is impregnated with an aqueous solution obtained by dissolving ethanol amine in a water slurry of silver oxalate, dried, and then heat-treated in a current of air. Separately, the α-alumina mentioned above in impregnated with an aqueous amide compound solution prepared by dissolving an amide compound in water and then dried. Subsequently, this α-alumina is immersed in a solution of cesium carbonate in ethanol, deprived of excess solution, and dried in nitrogen to obtain an amide compound-containing silver catalyst (Example 1 refers).

(2) α-Alumina is impregnated with an aqueous solution obtained by dissolving an amide compound in water and dried, for example, at 120° C. for 5 hours. Separately, the α-alumina mentioned above is impregnated with an aqueous solution which is separately prepared by dissolving ethanol amine in a water slurry of silver oxalate, and then subjected to a heat treatment. For example, the impregnated α-alumina is heated at 90° C. for 1 hour and then heated in a current of air by the use of a hot air drier at 200° C. for ten minutes and further at 300° C. for 10 minutes. Subsequently, this α-alumina is immersed in a solution of cesium carbonate in ethanol, deprived of excess solution, and dried in a stream of nitrogen to obtain an amide compound-containing silver catalyst. Incidentally, the temperature used for the drying in the stream of nitrogen is preferred to avoid surpassing 20° C.

(3) α-Alumina is impregnated with a solution prepared by adding an amide compound dissolved in water to a water slurry of silver oxalate, further adding ethanol amine thereto, and dissolving them altogether. Then the impregnated α-alumina is heat-treated. For example, the impregnated α-alumina is heated at 90° C. for 1 hour and then heated in a current of air by the use of a hot air drier at 200° C. for 10 minutes and further at 300° C. for 10 minutes. Subsequently, this α-alumina is immersed in a solution of cesium carbonate in ethanol, deprived of excess solution, and dried in a stream of nitrogen to obtain an amide compound-containing silver catalyst. Incidentally, the temperature used in the impregnation and that used in the drying in the stream of nitrogen are preferred to avoid surpassing 30° C.

(4) α-Alumina is impregnated with a solution obtained by adding an aqueous oxamide solution and an aqueous cesium carbonate solution to a water slurry of silver oxalate, further adding ethanol amine thereto, and dissolving them altogether. Then, the impregnated α-alumina is subjected to a heat treatment which is performed, for example, at 90° C. for 1 hour and subsequently in the open air by the use of a hot air drier at 200° C. for 10 minutes and further at 300° C. for 10 minutes to obtain an amide compound-containing silver catalyst.

(5) α-Alumina is impregnated with a solution of obtained by dissolving ethanol amine in a water slurry of silver oxalate and then subjected to a heat-treatment. This heat treatment is performed, for example, at 90° C. and then a current of air by the use of a hot air drier at 200° C. for 10 minutes and further at 300° C. for 10 minutes. Subsequently, the α-alumina mentioned above is impregnated with an aqueous solution obtained by dissolving an amide compound and cesium carbonate in water and then dried, for example, at 120° C. for 5 hours to obtain an amide compound-containing catalyst.

(6) α-Alumina is impregnated with an aqueous solution obtained by dissolving ethanol amine in a water slurry of silver oxalate and then subjected to a heat treatment which is performed, for example, at 90° C. for 1 hour and then in the open air by the use of a hot air drier at 200° C. for 10 minutes and further at 300° C. for 10 minutes. Subsequently, the α-alumina mentioned above is impregnated with a solution of cesium carbonate in ethanol, deprived of excess solution, and then dried in a stream of nitrogen. The temperature used during this drying in the stream of nitrogen is preferred to be adjusted so as to avoid surpassing 20° C. Then, the α-alumina mentioned above is impregnated with the aqueous solution of an amide compound and dried, for example, at 120° C. for 5 hours to obtain an amide compound-containing silver catalyst.

In the methods (2)–(4) mentioned above, when the heat treatment is performed in the open air, for example, at 200° C. and further at 300° C., the amide compound of certain species has the possibility of being scattered to the extent of rendering the deposition thereof infeasible or the adjustment of the amount of its deposition difficult, in the method (5), it possibly becomes difficult to attain uniform deposition of cesium as a reaction promoter on the catalyst because the solvent to be used requires to possess a high solubility for the cesium (alkali metal) and the drying also requires to be performed at a high temperature. In the method (6), the uniform deposition of cesium on the catalyst or the adjustment of the amount of deposition thereof may possibly become difficult because the cesium carbonate deposited in advance on the catalyst is inevitably dissolved when the α-alumina carrier is impregnated with the aqueous amide compound solution.

In contrast, in case of the method (1), the cesium (alkali metal) can be uniformly dispersed and deposited on the catalyst because the α-alumina is preparatorily made to carry silver and an amide compound thereon and then the α-alumina carrier mentioned above is immersed in a solution of the cesium in a solvent of low solubility such as, for example, ethanol and consequently enabled to induce adsorption of cesium thereto and further deprived of the solvent at a low temperature.

By the methods described above, it is made possible to obtain a silver catalyst which allows the amount of chlorine suffered to adhere thereto after the duration of the vapor phase oxidation of ethylene performed under the conditions mentioned above has totalled 240 hours from the start of the reaction to be decreased to about 0.1 mol. % per mol of silver. The use of the silver catalyst which has the amount of adhering chlorine in the range of 0.1–2 mol %, preferably 0.1–1.5 mol most of preferably 0.1–1 mol %, per mol of silver permits ethylene oxide to be continuously produced at a high selectivity for a long time.

The silver catalyst incorporating an organic nitrogen compound therein according to this invention is produced by the steps of (a) preparing an aqueous silver-amine complex solution by adding an aqueous amine complex solution to a water slurry containing a silver salt, (b) impregnating a porous carrier with the aqueous silver-amine complex solution and then subjecting the carrier impregnated with the aqueous solution to a heat treatment, (c) impregnating the heat-treated porous carrier with a solution of an organic nitrogen compound and then causing impregnated with the solution to dry, and (d) causing the carrier consequently incorporated the organic nitrogen compound to be impregnated with a solution of an alkali metal and then drying the wet impregnated carrier.

The silver salt, amine complex-forming agent, porous carrier, and alkali metal salt to be used herein may be those which are generally adopted in the preparation of a catalyst intended for the production of ethylene oxide. As typical examples of the silver salt, silver nitrate, silver acetate, and silver oxalate may be cited. As typical examples of the amine type complex-forming agent, mono-, di-, and triethanol amines may be cited. As a typical example of the porous carrier, α-alumina may be cited. Among other species at α-alumina, the α-alumina which has a specific surface area determined by the BET method in the range of 0.1–5 m$^2$/g, preferably 0.2–3 m$^2$/g, and an apparent porosity in the range of 25–70%, preferably 35–70%. As a typical example of the alkali metal salt, cesium carbonate may be cited.

An amount of the supported silver to the carrier is 5 to 25% by weight, preferably 5 to 20% by weight, most preferably 5 to 18% by weight per total weight of the catalyst. An alkali metal is usually incorporated as a promoter into the silver catalyst in accordance with the present invention and the amount thereof is 0.0004 to 0.04% by weight, preferably 0.0008 to 0.02% by weight, most preferably 0.001 to 0.01% by weight to silver per kg of finished catalyst. Among these alkali metals, cesium is the most preferable.

Now, the steps (a)–(d) mentioned above will be described more specifically below by citing a case of using silver oxalate as a silver salt, ethanol amine as an amine complex-forming agent, α-alumina as a porous carrier, cesium carbonate as an alkali metal salt, and an amide compound as an organic nitrogen compound.

Step (a)

An aqueous silver-amine complex solution is prepared by adding ethanol amine to a water slurry containing silver oxalate and allowing the silver oxalate to be thoroughly dissolved therein. Concerning the proportion of the amount of the ethanol amine to that of the silver oxalate, the ethanol amine to be used accounts for a proportion in the approximate range of 1–2 mols per mol of silver. Though the water slurry containing the silver oxalate uses water as a solvent, it may additionally use an alcohol such as methanol.

Step (b)

The aqueous silver-amine complex solution obtained at the step (a) is used for impregnating α-alumina. For the purpose of enabling this impregnation to proceed effectively, the α-alumina is preferred to be heated in advance. After the impregnation is completed, the impregnated α-alumina is generally heated at a temperature of not more than 100° C. to induce removal of water to a certain extent by vaporization. Then, this α-alumina is heat-treated to induce precipitation of silver by way of the so-called activating treatment.

The activating treatment mentioned above can be implemented by the method generally adopted in the manufacture of a catalyst intended for the production of ethylene oxide. As disclosed in JP-A-62-114,654, for example, the activation can be accomplished by heating the α-alumina in a current of air in one continuous step or in two separate steps at a temperature of normal temperature to 400° C., preferably normal temperature to 300° C. Specifically, this heating may be satisfactorily implemented by the use of a hot air drier which is operated with heated air to heat the carrier, for example, at 200° C. for about 10 minutes and further at 300° C. for about 10 minutes.

Step (c)

An amide compound solution is prepared by dissolving an amide compound in a solvent, preferably water or a mixture of water with an alcohol such as, for example, ethanol. This amide compound solution is used for impregnated the α-alumina has undergone the heat treatment at the step (b). The impregnated α-alumina is dried by being properly heated.

Step (d)

A cesium-containing solution is prepared by dissolving cesium carbonate in a solvent, preferably an alcohol such as, for example, ethanol. The α-alumina obtained at the step (c) is immersed in the solution and then dried preferably in a stream of an inert gas to obtain an amide compound-containing silver catalyst.

The silver catalyst of this invention can be otherwise obtained by any of the following methods.

(1) α-Alumina is impregnated with an aqueous solution of an amide compound and dried, for example, at 120° C. for 5 hours. Separately, the α-alumina mentioned above is impregnated with an aqueous solution, of which is separately prepared by dissolving ethanolamine in a water slurry of silver oxalate and then subjected to a heat treatment. For example, it is heated at 90° C. for 1 hour and then heated in a current of air by the use of a hot air drier at 200° C. for 10 minutes and further at 300° C. for 10 minutes. Subsequently, this α-alumina is immersed in a solution of cesium carbonate in ethanol, deprived of excess solution, and then dried in a stream of nitrogen to obtain an amide compound-containing silver catalyst. The temperature used for the drying in the stream of nitrogen is preferred to avoid surpassing 20° C.

(2) α-Alumina is impregnated with a solution prepared by adding a solution of an amide compound in water to a water slurry of silver oxalate, further adding ethanol thereto, and dissolving them altogether and the impregnated α-alumina is subjected to a heat treatment. This heat treatment is performed, for example, at 90° C. for 1 hour and then in the open air by the use of a hot air drier at 200° C. for ten minutes and further at 300° C. for 10 minutes. Subsequently, this α-alumina is immersed in a solution of cesium carbonate in ethanol, deprived of excess solution, and then dried in a stream of nitrogen to obtain an amide compound-containing silver catalyst. The temperature used for the immersion and that for drying in the stream of nitrogen are preferred to avoid surpassing 20° C.

(3) An aqueous solution of oxamide and an aqueous solution of cesium carbonate are added to a water slurry of silver oxalate, ethanolamine is further added thereto, and they are dissolved altogether. α-Alumina is impregnated with the resultant solution and then subjected to a heat treatment. This heat treatment is implemented, for example, at 90° C. for 1 hour and then in a current of air by the use of a hot air drier at 200° C. for 10 minutes and further at 300° C. for 10 minutes.

(4) α-Alumina is impregnated with a solution obtained by dissolving ethanol amine in a water slurry of silver oxalate and then subjected to a heat treatment. This heat treatment is implemented, for example, at 90° C. for 1 hour and then in a current of air by the use of a hot air drier at 200° C. for 10 minutes and further at 300° C. for 10 minutes. Thereafter, the α-alumina mentioned above is impregnated with an aqueous solution obtained by dissolving an amide compound and cesium carbonate in water and then dried, for example, at 120° C. for 5 hours to obtain an amide compound-containing silver catalyst.

(5) α-Alumina is impregnated with an aqueous solution obtained by dissolving ethanol amine in a water slurry of silver oxalate and then subjected to a heat treatment. This heat treatment is carrier out, for example, at 90° C. for 1 hour and then in a current of air by the use of a hot air drier at 200° C. for 10 minutes and further at 300° C. for 10 minutes. Subsequently, the α-alumina mentioned above is immersed in a solution of cesium carbonate in ethanol, deprived of excess solution, and then dried in a stream of nitrogen. The temperature used in this case is preferred to be adjusted so as to avoid surpassing 20° C. Then, the α-alumina mentioend above is impregnated with an aqueous solution of an amide compound and dried, for example, at 120° C. for 5 hours to obtain an amide compound-containing silver catalyst.

In the method (1–(3) mentioned above, when the heat treatment is performed in the open air, for example, at 200° C. and further at 300° C., the amide compound of certain species has the possibility of being scattered to the extent of rendering the incorporation thereof infeasible or the adjustment of the amount of its incorporation difficult. In the method (4), it possibly becomes difficult to attain uniform deposition of cesium as a reaction promoter on the catalyst because the solvent to be used requires to possess a high solubility for the cesium (alkali metal) and the drying also requires to be performed at a high temperature. In the method (5), the deposition of cesium on the catalyst or the adjustment of the amount of deposition thereof may possibly become difficult because the cesium carbonate deposited in advance on the catalyst is inevitably dissolved when the α-alumina carrier is impregnated with the aqueous amide compound solution.

In contrast, the method of this invention permits uniform dispersion and deposition of cesium on the catalyst because the deposition of silver and an amide compound on the α-alumina precedes the immersion of the α-alumina in a solution of cesium in a solvent of low solubility such as, for example, ethanol and the consequent adsorption of cesium to the α-alumina and the impregnated α-alumina is thereafter deprived of the solvent at a low temperature.

Incidentally, the α-alumina which is used as a porous carrier is preferred to have a specific surface area determined by the BET method in the range of 0.1–5 $m^2/g$, preferably 0.2–3 $m^2/g$, and an apparent porosity in the range of 25–70%, preferably 35–70%.

The silver catalyst of this invention is suitable for the production of ethylene oxide by the vapor phase oxidation of ethylene. This vapor phase oxidation of ethylene can be accomplished by adopting any of the methods heretofore known to the art while using the silver catalyst of this invention instead.

The standard conditions which prevail in the production on a commercial scale, namely a reaction temperature in the range of 150°–300° C., preferably 180°–280° C., a reaction pressure in the range of 2–40 $kg/cm^2$ G, preferably 10–30 $kg/cm^2$ G, and a space velocity in the range of 1,000–30,000 $hr^{-1}$ (STP), preferably 3,000–8,000 $hr^1$ (STP). As respects the composition of the feed gas which is passed through the catalyst, the method of using 0.5–30 vol. % of ethylene, 5–30 vol. % of carbon dioxide gas, and the balance of such an inert gas as, for example, nitrogen, argon, or steam and further using a lower hydrocarbon such as methane or ethane and, as a reaction inhibitor, 0.1–10 ppm (by volume) of an organic chloride compound such as ethylene dichloride or ethyl chloride can be suitably adopted.

As typical examples of the molecular oxygen-containing gas to be used in this invention, air, oxygen, and enriched air may be cited.

The conversion and the selectivity which are indicated in the working examples and the control represent the magnitudes which have been calculated in accordance with the following formulas.

Conversion (%)=[(Number of mols of reacted ethylene)/(Number of mols of ethylene in the feed gas)]×100

Selectivity (%)=[(Number of mols of ethylene converted to ethylene oxide)/(Number of mols of reacted ethylene)]×100.

Now, this invention will be described more specifically below with reference to working examples. The letter "L" stands for liter.

EXAMPLE 1

<Preparation of catalyst>

Catalyst according to this invention (Catalyst A)

To a water slurry containing 420 g of silver oxalate, 360 g of ethanolamine was added as kept cooled in a water bath so as to effect thorough solution of the silver oxalate. The resultant aqueous solution was used for impregnating an α-alumina carrier (having an apparent porosity of 55% and a BET specific surface area of 0.70 $m^2/g$) heated in advance to 80° C. and the impregnated carrier was heated at 90° C. for 1 hour. The composite consequently obtained was heated at 200° C. for 10 minutes by the use of a perforated belt type hot air drier adapted to feed air at a rate of 0.5 m/second and then heated further at 300° C. for 10 minutes. An aqueous oxamide solution prepared separately by dissolving 244 g of oxamide in water was used for impregnating the α-alumina carrier which had undergone the treatment described above and dried at 120° C. for 5 hours. Then, the α-alumina carrier so treated was immersed in a solution of 1.16 g of cesium carbonate in 1580 ml of guaranteed grade ethanol and left standing therein at 20° C. for 3 hours. Thereafter, the wet carrier was deprived of excess solution and dried thoroughly by being swept with dry nitrogen supplied at a rate of 50 L/minute for 5 hours to prepare the catalyst A. In this while, the temperature was kept from surpassing 20° C. Silver content and cesium content in the catalyst were respectively 13.5% by weight and $3.51 \times 10^{-3}$ gram equivalent/kg-catalyst.

Control.

Catalyst for comparison (Catalyst B)

The catalyst B was prepared by faithfully following the procedure used for the preparation of the catalyst A while using an aqueous oxamide solution prepared by dissolving 0.244 g of oxamide in water for impregnating the treated α-alumina carrier and drying the impregnated carrier at 120° C. for 5 hours. Silver content and cesium content in the catalyst were respectively 13.5% by weight and $3.51 \times 10^{-3}$ gram equivalent/kg catalyst.

<Evaluation of efficiency>

A reaction tube of stainless steel provided with an outer heating device and measuring 25 mm in inside diameter and 6000 mm in length as loaded with a sample, i.e. 2.2 L of the catalyst A (or the catalyst B). To this reaction tube kept under a reaction pressure of 15 $kg/cm^2$ G, a feed gas composed of 20 vol. % of ethylene, 8 vol. % of oxygen, 7 vol. % of carbon dioxide, 0.1 vol. % of ethane, 2.0 ppm of ethylene dichloride, and the balance of methane, nitrogen, and argon was introduced at a space velocity of 6500 $hr^{-1}$. The reaction tube thus operated was gradually heated so that the conversion of ethylene reached 11 mol. % after the duration of the supply of the feed gas totalled eight days. When the reaction temperature was raised to 234° C., the ethylene conversion reached 11 mol %. Incidentally, the reaction temperature was 190° C. when the reaction was started. Thereafter, the reaction was continued for ten days with the reaction temperature adjsuted so as to keep the conversion of ethylene at 11 mol. %. The fact that the conversion of ethylene was not changed in this while means that the reaction temperature was maintained at 234° C.

After the reaction was completed, the catalyst bed in the reaction tube was divided into five substantially equal portions and the portions were sequentially extracted from the reaction tube. The portions of the catalyst was tested for the amount of chlorine adhering to the catalyst by the use of a fluorescent X-ray analyzer (made by Rigaku Denki Kogyo Co., Ltd. and sold under the trademark designation of "TKF-3063"). The results obtained of the 5 portions were averaged and the average thus found was reported as the total amount of chlorine adhering to the whole catalyst.

The amounts of chlorine (per mol of silver) adhering to the catalyst A and the catalyst B were as follows.

Catalyst A: 0.3 mol. %
Catalyst B: 3.0 mol. %

<Comparison of efficiency between the catalyst A and the catalyst B>,

In the same manner as in the evaluation of efficiency mentioned above, the reaction was continued for 50 days and for one year respectively as reckoned from the start of reaction. The reaction temperature was so adjusted as to keep the conversion of ethylene at 11 mol. %. The difference in selectivity and the difference in reaction temperature between the reaction continued for 50 days and the reaction continued for one year were as follows.

Catalyst A:
  Difference in selectivity=−0.5 mol. %
  Difference in reaction temperature=+2° C.
Catalyst B:
  Difference in selectivity=−2.0 mol. %
  Difference in reaction temperature=+5° C.

The catalyst A, for the purpose of keeping the conversion of ethylene at 11 mol. % at the end of 1 year's reaction, had only to increase the reaction temperature by 2° C. over the reaction temperature at the end of 50 days' reaction and had suffered a decrease of only 0.5 mol. % in the selectivity as compared with that obtained at the end of 50 days' reaction. In contrast, the catalyst B, for the purpose of keeping the conversion of ethylene at 11 mol. % at the end of one year's reaction, had to increase the reaction temperature by 5° C. over the reaction temperature at the end of 50 days' reaction and had suffered a decrease of as much as 2 mol. % as compared with that obtained at the end of 50 days' reaction.

From the results, it is noted that the catalyst A enjoyed a satisfactory service life and exhibited high selectivity over a long period as compared with the catalyst B for comparison (conventional product).

EXAMPLES 2–6

Catalysts were prepared by following the procedure of Example 1 adopted for the preparation of the catalyst A while using propionamide, formamide, malonamide, lactamide, and urea respectively in the amounts indicated in Table 1 in the place of oxamide. Silver content and cesium content were respectively 13.5% by weight and 3.51×10$^{-3}$ gram equivalent/kg-catalyst.

In the same manner as used for the evaluation of efficiency in Example 1, these catalysts were tested for the amounts of chlorine suffered to adhere thereto after 240 hours' reaction.

The reactions using these catalysts in the same manner as adopted for the comparison of efficiency between the catalyst A and the catalyst B in Example 1 were continued for 50 days and for one year and the difference in selectivity and the difference in reaction temperature between the reaction continued for 50 days and the reaction continued for one year.

The results of the experiment are shown in Table 1 together with the results obtained of Example 1 using oxamide.

TABLE 1

| Example | Kind of amide compound | Amount charged (g) | Atomic ratio of contents (N/Ag) | Amount of chlorine suffered to adhere (mol % per mol of Ag) | Change in quality of catalyst | |
|---|---|---|---|---|---|---|
| | | | | | Selectivity (mol %) | Temperature (° C.) |
| 1 | Oxamide | 0.244 | 0.002 | 0.3 | −0.5 | +2 |
| 2 | Propionamide | 1.213 | 0.006 | 0.5 | −0.5 | +2 |
| 3 | Formamide | 0.747 | 0.006 | 0.9 | −0.6 | +2 |
| 4 | Malonamide | 0.847 | 0.006 | 1.0 | −0.7 | +3 |
| 5 | Lactamide | 1.476 | 0.006 | 1.1 | −0.8 | +4 |
| 6 | Urea | 0.499 | 0.006 | 1.0 | −0.7 | +3 |
| Control | None | — | — | 3.0 | −2.0 | +5 |

Change in quality:
Reaction temperature: (Reaction temperature required for keeping the conversion of ethylene at 11 mol. % at the end of one year's reaction)—(Reaction temperature required for keeping the conversion of ethyene at 11 mol. % at the end of 50 days' reaction).
Selectivity: (Selectivity of ethylene oxide at the end of one year's reaction)—(Selectivity of ethylene oxide at the end of 50 days' reaction).

What is claimed is:

1. A method for the production of ethylene oxide, which comprises effecting vapor phase oxidation of ethylene oxide with a molecular oxygen-containing gas in the presence of a silver catalyst by performing vapor phase oxidation of ethylene such that an amount of chlorine suffered to adhere thereto is not more than 2 mol % per mol of silver after the duration of the reaction caused under the following condition has totaled 240 hours from the start of the reaction:

(Conditions for vapor phase oxidation)
  Reaction tube: Made of stainless steel and measuring 25 mm in inside diameter and 6000 mm in length
  Amount of catalyst loaded: 2.2 liters
  Reaction pressure: 15 Kg/cm$^2$ G
  Reaction temperature: Such a temperature as attains ethylene conversion, 11 mol %
  Composition of feed gas: Ethylene 20 vol. %, oxygen 8 vol. %, carbon dioxide 7 vol. %, ethane 0.1 vol. %, ethylene dichloride 2.0 ppm, and at least one inert gas selected from among methane, nitrogen, and argon
  Gas hourly space velocity of gas: 6500 hr$^{-1}$.

2. A method for the production of ethylene oxide, which comprises effecting vapor phase oxidation of ethylene with a molecular oxygen-containing gas in the presence of a silver catalyst incorporating an organic nitrogen compound therein.

3. A method according to claim 1, wherein the amount of chlorine suffered to adhere thereto is in the range of 0.1–1.5 mol % per mol of silver.

4. A method according to claim 1, wherein a carrier therefore is α-alumina, said carrier supports silver thereon in an amount in the range of 2–25% by weight per total weight of the catalyst, and said carrier further supports an alkali metal thereon in an amount in the range of 0.0004–0.04 gram equivalent weight per kg of finished catalyst.

5. A method according to claim 4, wherein said alkali metal is cesium.

6. A method according to claim 4, wherein said carrier has a BET specific surface area in the range of 0.1–5 m$^2$/g and an apparent porosity in the range of 25–70%.

7. A method according to claim 2, wherein the content of said organic nitrogen compound is such that the atomic ratio of nitrogen atom (N): silver atom (Ag) falls in the range of 0.00005:1–0.5:1.

8. A method according to claim 2, wherein said organic nitrogen compound is an amide compound.

9. A method according to claim 4, wherein said amide compound is at least one member selected from the group consisting of formamide, propionamide, oxamide, malonamide, lactamide, and urea.

* * * * *